United States Patent [19]  
Rasmussen

[11] 4,025,517  
[45] May 24, 1977

[54] 4-OXO-2-HEXAHYDROPYRIMIDINYLI-DENE UREAS

[75] Inventor: Chris Royce Rasmussen, Ambler, Pa.

[73] Assignee: McNeil Laboratories, Incorporated, Fort Washington, Pa.

[22] Filed: June 7, 1976

[21] Appl. No.: 693,449

Related U.S. Application Data

[60] Division of Ser. No. 589,494, June 23, 1975, Pat. No. 3,983,135, which is a continuation-in-part of Ser. No. 508,795, Sept. 23, 1974, abandoned, which is a continuation-in-part of Ser. No. 408,022, Oct. 19, 1973, abandoned.

[52] U.S. Cl. .............. 260/256.4 C; 260/309.7; 424/251; 424/273

[51] Int. Cl.$^2$ .................. C07D 239/22

[58] Field of Search .............. 260/256.4 C

[56] References Cited

UNITED STATES PATENTS

| 3,105,077 | 9/1963 | Muller et al. | 260/256.4 C |
| 3,168,520 | 2/1965 | Kleeman et al. | 260/309.7 |
| 3,772,292 | 11/1973 | Martin et al. | 260/256.4 C |

Primary Examiner—Donald G. Daus  
Assistant Examiner—James H. Turnipseed  
Attorney, Agent, or Firm—Geoffrey G. Dellenbaugh

[57] ABSTRACT

Compounds of the class of 4-oxo-2-imidazolidinylidene ureas and 4-oxo-2-hexahydropyrimidinylidene ureas, useful as anti-secretory agents and central nervous system (CNS) depressants.

1 Claim, No Drawings

4-OXO-2-HEXAHYDROPYRIMIDINYLIDENE UREAS

CROSS-REFERENCE TO RELATED APPLICATIONS

This is a division of application Ser. No. 589,494 filed June 23, 1975, now U.S. Pat. No. 3,983,135 which in turn is a continuation-in-part of my application Ser. No. 508,795, filed Sept. 23, 1974, now abandoned, which in turn is a continuation-in-part of my application Ser. No. 408,022, filed Oct. 19, 1973, now abandoned.

DESCRIPTION OF THE PREFERRED EMBODIMENTS

The novel 4-oxo-2-imidazolidinylidene ureas and 4-oxo-2-hexahydropyrimidylidene ureas of this invention may be structurally represented by the formulas:

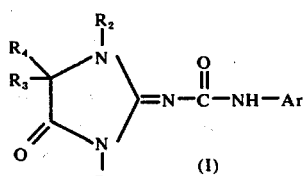

and

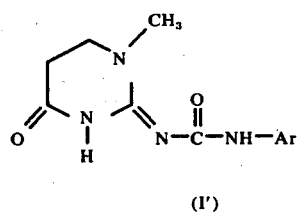

wherein $R_1$ is a member selected from the group consisting of hydrogen and loweralkyl, preferably hydrogen; $R_2$ is a member selected from the group consisting of hydrogen and loweralkyl, preferably methyl; $R_3$ is a member selected from the group consisting of hydrogen and aryl, preferably hydrogen; $R_4$ is a member selected from the group consisting of hydrogen, aryl, and arylalkyl, preferably hydrogen; and Ar is aryl; provided that said $R_3$ and said $R_4$ are other than 2,6-disubstituted aryl. This restriction on the identity of $R_3$ and $R_4$ is imposed because the steric hindrance occurring if $R_3$ and $R_4$ are not so restricted makes preparation of such compounds difficult.

As used herein, "loweralkyl" and "loweralkoxy" may be straight or branch chained and have from 1 to about 8 carbon atoms, such as, for example, methyl, ethyl, propyl, isopropyl, butyl, pentyl, octyl, and the like alkyls, and respectively, the corresponding alkoxys such as methoxy, ethoxy, etc. The term "halo" is generic to fluoro, bromo, chloro and iodo.

The term "aryl" includes phenyl, nitrophenyl, trifluoromethylphenyl, diloweralkylaminophenyl, and phenyl substituted with one to three members each selected from the group consisting of halo, loweralkyl, and loweralkoxy. The term "arylalkyl" means benzyl, phenethyl, phenpropyl, and the like arylalkyls, but the preferred arylalkyl is benzyl.

The compounds of formula (I) wherein either $R_1$ or $R_2$ (or both) are hydrogen may exist in several tautomeric forms besides that represented by formula (I). These forms are represented by the following:

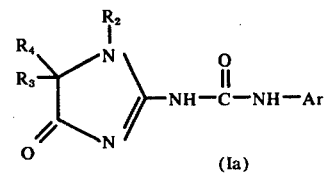

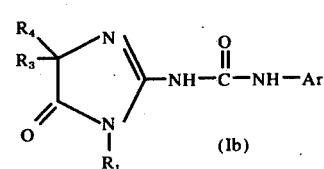

wherein $R_1$, $R_2$, $R_3$, $R_4$ and Ar are as previously defined. The compounds of formula (I') may likewise exist in two similar tautomeric forms.

The 4-oxo-2-imidazolidinylidene ureas of formula (I) are readily obtained by the reaction of an appropriate 2-imino-imidazolidin-4-one (II) with an appropriate aryl isocyanate (III). A slight stoichiometric excess of the former reactant is preferred to ensure complete reaction with the aryl isocyanate. The reaction is preferably conducted in an anhydrous, polar, inert, aprotic, organic solvent such as, for example, a polyethereal solvent, e.g., dioxane, tetrahydrofuran (THF), 1,2-dimethoxy-ethane, the dimethyl ether of diethylene glycol, and the like; N,N-dimethylformamide (DMF); dimethyl sulfoxide (DMSO); hexamethylphosphoric acid triamide; and other similar organic solvents. Any excess 2-imino-1-R-imidazolidin-4-one reactant (II) is filtered off after the reaction is completed and the desired product is generally recovered by the addition of cold water to the reaction mixture. The crude precipitated product may then be purified by standard recrystallization techniques from suitable organic solvents. In cases where the purified product is obtained in large crystalline form, it may be pharmaceutically advantageous to reduce the size of the crystals by standard techniques known in the art, i.e., milling, micronization, reprecipitation, etc. These techniques are known to result in enhanced absorption and bioavailability of a given medicament.

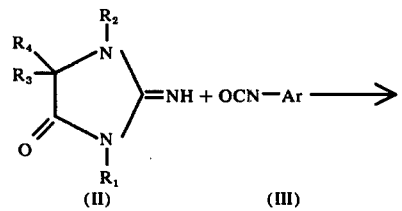

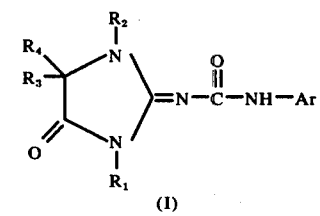

In a completely analogous manner, the 4-oxo-2-hexahydro-pyrimidinylidene ureas of formula (I') may be obtained by the reaction of an 2-imino-1-methyl-hexahydropyrimidin-4-one (II') with an appropriate aryl isocyanate (III). This reaction is illustrated by the following:

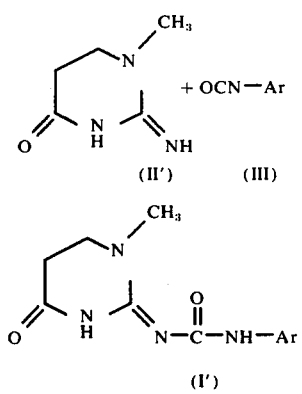

The subject compounds of formulas (I) and (I') have been found to possess useful anti-secretory activity by the following acute gastric fistula rat test. The anti-secretory activity of the compound to be tested is studied in female Sprague-Dawley rats after intraduodenal (i.d.) injection of the compound of doses generally ranging from 2.5–40 mg/kg body weight. The rats are fasted 24 hours before testing and are given water ad libidum while being kept in individual cages. On the day of testing, the rats are weighed and are selected so that the rats in each test have weights within a range of ±20 g.

Surgery is carried out under light ether anesthesia. As soon as the rat is anesthetized, its teeth are removed, using a small pinch pliers. A mid-line incision is made on the abdoment about 1½ cm in length and the stomach and duodenum are exposed. If at this point the stomach is filled with food or fecal material, the rat is discarded. Using 4-0 MERSILENE* Suture, a purse string stitch is placed on the fundic portion of the stomach taking care not to pierce any blood vessels in the area. A small nick is made into the stomach in the center of the purse string, and a cannula, consisting of a small vinyl tube with a flange on one end, it put into the stomach and the purse string stitch is closed tightly around the flange. Immediately following this, the test compound is administered I.D. in a volume of 0.5 ml per 100 gm rat. Three rats are generally used for each drug dose tested. Control rats receive the test vehicle, usually 0.5% aqueous methyl cellulose.

*Trademark of Johnson & Johnson or Subsidiary.

After administration of the test compound, the abdominal wall and skin are closed simultaneously with 3 to 4 18 mm wound clips and a collecting tube is placed on the cannula. Each rat is then placed in a box in which a longitudinal slit has been made to allow the cannula to hang freely and to allow the rat to move about unencumbered. After the rat is allowed to stabilize for 30 minutes, the collection tube on the cannula is discarded and replaced with a clean tube to receive the gastric juice. Collections are made at 1 hour. At the end of the study, the cannula is removed and the rat is sacrificed.

The sample of gastric contents collected is drained into a centrifuge tube and centrifuged to pack down the sediment. Volumes are read and a 1 ml aliquot of the supernatant is put into a beaker containing 10 ml distilled $H_2O$ and is titrated to pH7 using 0.01NaOH. Results are determined for Volume, Titratable Acid, and Total Acid Output where Volume = total ml. of gastric juice minus sediment; Titratable Acid (milliequivalents/l)=amount of 0.01N NaOH needed to titrate the acid to pH7; and Total Acid Output= Titratable Acid × Volume. Results are reported in % Inhibition vs Controls.

The vast majority of the compounds of the invention exhibit useful anti-secretory activity as measured by the above test, particularly those compounds of formulas (I) and (I') wherein Ar is other than trisubstituted phenyl.

In addition, the subject compounds of formulas (I) and (I') have been found to possess useful CNS depressant properties as demonstrated in one or more of the following tests indicative of such activities on laboratory animals. Test A: An anti-anxiety assay as reported by I. Geiler in Psychosomatic Medicine, eds. J. H. Nadine and J. H. Moyer (Lea and Febiger, Phila.) p. 267 (1962) and modified by D. L. Margules and L. Stein in Psychopharmacologia (Berl.) 13, 74–80 (1968). The anti-anxiety activity of the compound to be tested is studied in rats daily for 5 days after intraperitoneal (i.p.) injection of the compound at doses generally ranging from 5–25 mg/kg body weight and the effect of the compound is observed on the animal's bar pressing rate while working for food reinforcement. Activity is also observed after oral administration of doses generally ranging from 5–25 mg./kg. body weight by the identical procedure. The method consists of determining the effect of a test compound on non-punished and punished responses. Hungry rats are trained to press a bar for food reinforcement: a dipper full of milk is delivered to the rat on the average of once every 2 minutes (variable interval schedule — V.I. II). Following 12 minutes on this schedule, a tone is presented for 3 minutes which signals the rewarding and simultaneous punishment of each bar press (a dipper full of milk is presented and accompanied by a shock, delivered through the grid floor, with each bar press). The shock delivered is 0.2 milli-seconds in duration and ranges in intensity from 0.5 to 3.5 milli-amperes. Each rat is presented with 4 to 6 alternating pairs of unpunished periods when milk alone is given and punished periods when milk and shock are administered. Control responses are obtained for each rat after saline intraperitoneal injection daily for 5 days. Each rat is evaluated at the same time of day and in the same test chamber. Responses are recorded and reinforcements (milk) and punishment (shock) delivered by means of suitable automated equipment. The activity of the compound to be tested is evaluated by comparing the number of bar presses after placebo administration with the number after administration of the compound in each rat.

Test B: A muscle-relaxant assay as judged by the effect of the compound to be tested on strychnine-induced seizures as described by M. J. Orloff et al., Proc. Soc. Exp. Biol. and Med. 70, 254 (1949) as modified by G. Chen and B. Bohner, J. Pharmacol. and Expt. Therap. 117, 142 (1956). The anti-syrychnine activity is observed in mice at oral doses of about 25–500 mg./kg. body weight by determining the effect of the compound on the seizure threshold induced by strychnine.

Test C: A mouse behavioral assay as described by S. Irwin, Gordon Research Conference on Medicinal Chemistry, 1959, p. 133. In this assay, such symptoms as ataxia, decrease in motor activity and loss of righting reflex are observed after intraperitoneal (i.p.) administration in mice of the compound to be treated at doses ranging from 10-300 mg./kg. body weight.

In view of the foregoing, an effective CNS depressant amount of a compound of formula (I) or (I') intimately admixed with a pharmaceutically acceptable carrier may be systemically administered to warm-blooded animals, including humans, to elicit a CNS depressant response. When administering the hereinabove described dosage unit forms for such purpose, amounts of active ingredient ranging about 15-500 mg, and preferably about 15-250 mg, per dosage unit may be utilized.

Among the preferred compounds of the invention are those of formula (I) wherein $R_1$ $R_3$ $R_4$ hydrogen, $R_2$ is methyl, and Ar is

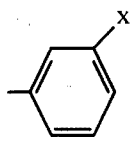

wherein X is a member selected from the group consisting of hydrogen, halo, methyl, ethyl, methoxy, ethoxy, and trifluoromethyl. The most preferred compounds of formula (I) are those wherein $R_1 = R_3 = R_4 =$ hydrogen, $R_2$ is methyl, and Ar is

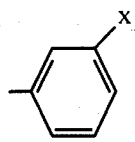

wherein X is a member selected from the group consisting of hydrogen, methyl, methoxy, chloro, bromo, and trifluoromethyl. These preferred compounds are especially useful for their anti-anxiety activity.

Accordingly, this invention provides a process of alleviating anxiety which comprises systemically administering to an anxious individual, for example, one whose anxiety inhibits his ability to cope with the various requirements of his daily life, or one whose anxiety would have an adverse effect on his physical well-being, an aforementioned compound as the active ingredient in a concentration adequate to elicit an effective anti-anxiety response. Preferably, dosage unit forms containing from about 15 to about 500 mg of such active ingredient are employed for anti-anxiety purposes. A suitable human regimen contemplated for the most preferred compounds disclosed above is 15 to 500 mg orally or parenterally administered three or four times a day.

For purposes of relaxing skeletal muscle, the preferred compounds of formula (I) are those wherein $R_1 = R_3 = R_4 =$ hydrogen, $R_2$ is methyl and Ar is a member selected from the group consisting of

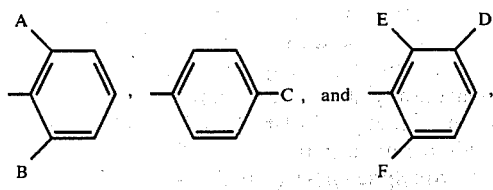

wherein A is a member selected from the group consisting of halo and loweralkyl; B is a member selected from the group consisting of halo and loweralkyl; C is a member selected from the group consisting of halo, loweralkyl, loweralkoxy, trifluoromethyl and dimethylamino; D is halo; E is loweralkyl; and F is loweralkyl.

Accordingly, this invention provides a process of alleviating muscular pain which comprises systemically administering to a subject with such pain, such as, for example, which may result from muscular spasm or chronic lower back pain, an aforementioned compound as the active ingredient in a concentration adequate to elicit an effective skeletal muscle relaxant response. Preferably, dosage unit forms containing from about 15 to about 500 mg of such active ingredient are employed for muscular relaxation purposes. A suitable human regimen contemplated for the preferred compounds disclosed above is 15 to 500 mg orally or parenterally administered three or four times a day.

The following examples are intended to illustrate and not to limit the scope of the present invention. Unless otherwise stated, all parts are by weight.

EXAMPLE I 1-m-Chlorophenyl-3-(1-methyl-4-oxo-2-imidazolidinylidene) urea

To a suspension of creatinine (5.66 g, 0.05 mole) in 150 ml. of dry dimethylformamide (DMF) is added 7.68 g. (0.05 mole) of m-chlorophenylisocyanate. The mixture is stirred for 2 hours and heated on a steam bath for 30 minutes. During this time the solution becomes clear (yellow). The solution is filtered and the filtrate cooled. Ice and ice-water are added to the filtrate. A light yellow solid precipitates and is filtered off. After recrystallizations from acetone-methanol and tetrahydrofuran-ether, the pure product, 1-m-chlorophenyl-3-(1-methyl-4-oxo-2-imidazolidinylidene)urea, is obtained, mp 180°-180.5° C.

Analysis: Calcd. for $C_{11}H_{11}ClN_4O_2$: C, 49.54; H, 4.16. Found: C, 49.45; H, 4.19%.

EXAMPLE II

1m-Chlorophenyl-3-(1-methyl-4-oxo-2-imidazolidinylidene) urea hydrate

About 120 g of pure 1-m-chlorophenyl-3-(1-methyl-4-oxo-2-imidazolidinylidine)urea obtained according to Example I is dissolved in 400 ml of DMF and poured with vigorous stirring into about 3.5 liters of water. The resultant fine crystals of 1-m-chlorophenyl-3-(1-methyl-4-oxo-2-imidazolidinylidene)ureahydrate are collected by filtration and washed well with water, dried at room temperature for 4 days followed by drying (room temperature) in vacuo at 5.0 mm for 8 hr; yield about 120 g; mp 180.5°-181.5° C.

Analysis: Calcd. for $C_{11}H_{11}ClN_4O_2 \cdot H_2O$: C, 46.41; H, 4.60; N, 19.68; $H_2O$, 6.33%. Found: C, 46.43; H, 4.62; N, 19.83; $H_2O$, 6.37, 6.59, 6.41%

EXAMPLE III 1-(2,6-Dichlorophenyl)-3-(1-methyl-4-oxo-2-imidazolidinylidene)urea

Following the procedure of Example I, but substituting an equivalent amount of 2,6-dichlorophenylisocyanate for the m-chlorophenylisocyanate used therein, 1-(2,6-dichlorophenyl)-3-(1-methyl-4-oxo-2-imidazolidinylidene) urea is obtained; m.p. 211°–212° C. dec.

Analysis: Calcd. for $C_{11}H_{10}Cl_2N_4O_2$: C, 43.87; H, 3.35%. Found: C, 43.55; H, 3.31%.

EXAMPLE IV 1-(1-Methyl-4-oxo-2-imidazolidinylidene)-3-p-methoxyphenyl urea

To a stirring suspension of creatinine (11.88 g, 0.105 mole) in 100 ml dry DMF, p-methoxyphenylisocyanate (14.91 g, 0.100 mole) is added dropwise over a period of about 15 minutes with cooling. After stirring for 8 hours, the mixture is poured into about 500 ml of ice water to yield white crystals of product which are filtered off, washed with water and purified by recrystallization (twice) from tetrahydrofuran-methanol. The crystalline product is reduced to finer size by adding a solution of the product in minimal DMF to vigorously stirred water (about 1.1 liters) and filtering off the resultant crystals which are then dried at room temperature in vacuo for 24 hours; m.p. 193°–5° C dec.

EXAMPLE V

Following the procedure of Example IV, but substituting equivalent amounts of an appropriate imidazolidin-4-one and an appropriate arylisocyanate, the following respective products are obtained:

1-(1-methyl-4-oxo-2-imidazolidinylidene)-3-(3,4-dichlorophenyl)urea hemihydrate; m.p. 199°–202° C. dec.;
1-(1-methyl-4-oxo-2-imidazolidinylidene)-3-m-methoxyphenylurea hydrate; m.p. 144° C.; and
1-m-chlorophenyl-3-(4-oxo-2-imidazolidinylidene)urea; m.p. 225°–227° C. dec.

EXAMPLE VI 1-(1-Methyl-4-oxo-2-imidazolidinylidene)-3-p-chlorophenylurea

To a stirring suspension of creatinine (11.88 g, 0.105 mole) in 100 ml dry DMF, p-chlorophenylisocyanate (15.36 g, 0.100 mole) is added dropwise with cooling. The mixture is stirred for 16 hours and then poured into about 500 ml of iced-water to yield the crystalline product which is filtered off, washed with water and recrystallized twice from acetone-methanol, one from tetrahydrofuran (THF) and then from DMF-methanol. The resultant pure 1-(1-methyl-4-oxo-2-imidazolidinylidene)3-p-chlorophenylurea is dried in vacuo for 24 hours; m.p. 190°–2° C dec.

EXAMPLE VII 1-(1-Methyl-4-oxo-2-imidazolidinylidene)-3-p-tolylurea

To a stirring suspension of creatinine (11.88 g, 0.105 mole) in 100 ml dry DMF, p-tolylisocyanate (13.31 g – 0.100 mole) is added dropwise over a period of about 15 minutes with cooling. After stirring for 3.5 hrs., the mixture is poured into about 500 ml iced-water to give white crystals of product which are filtered off and washed with water. Recrystallization of the product from acetone-methanol and then from THF-methanol affords the product, 1-(1-methyl-4-oxo-2-imidazolidinylidene)-3-p-tolyl urea. The crystalline particles are reduced to finer size by adding a solution of the thus-obtained product in minimal DMF to about 1.1 liters of vigorously stirring water, filtering off and drying the resultant fine crystals in vacuo for 24 hours; m.p. 198°–200° C dec.

EXAMPLE VIII 1-(1-Methyl-4-oxo-2-imidazolidinylidene)-3-m-tolylurea is obtained by repeating the procedure of Example VII with an equivalent amount of m-tolylisocyanate substituted for the p-tolylisocyanate used therein; reaction time is 6 hours; recrystallization twice from THF-methanol; m.p. 183°–185° C. dec.

EXAMPLE IX 1-(1-Methyl-4-oxo-2-imidazolidinylidene)-3-m-trifluoromethyl-phenylurea is obtained by repeating the procedure of Example VII with an equivalent amount of m-trifluorophenylisocyanate substituted for the p-tolylisocyanate used therein; reaction time is 6 hours; recrystallization from acetone-methanol; m.p. 197°–8° C dec.

EXAMPLE X 1-(1-Methyl-4-oxoimidazolidinylidene)-3-(2,6-xylyl)urea

A suspension of 5.66 g (0.05 mole) of creatinine and 7.36 g (0.05 mole) of 2,6-xylylisocyanate in 200 ml of dry THF is heated under reflux overnight (about 15 hours). The hot solution is filtered and the filtrate diluted with ether to about 400 ml total volume, giving the crude product. Recrystallization from methanol affords pure 1-(1-Methyl-4-oxoimidazolidene)-3-(2,6-xylyl) urea, m.p. >190° C dec.

Analysis: Calcd. for $C_{13}H_{16}N_4O_2$ (260.39): C, 59.98; H, 6.20%. Found: C, 60.17; H, 6.24%.

EXAMPLE XI 1-(1-Methyl-4-oxo-2-imidazolidinylidene)-3-phenylurea

The procedure of Example IV is followed except that an equivalent amount of phenylisocyanate is substituted for the p-methoxyphenyl-isocyanate used therein to yield as final product: 1-(1-methyl-4-oxo-2-imidazolidinylidene)-3-phenylurea. m.p. (185°) 187°–9° C.

EXAMPLE XII

By repeating the procedure of Example VI, except that an equivalent amount of an appropriate 2-imino-1-loweralkyl-imidazolidin-4-one and an appropriate aryl isocyanate are utilized as reactants, the following respective products are obtained:

1-(1-ethyl-4-oxo-2-imidazolidinylidene)-3-phenyl urea;
3-m-bromophenyl-1-(1-methyl-4-oxo-2-imidazolidinylidene) urea, m.p. 183°–184° C dec;
3-p-ethoxyphenyl-1-(1-n-octyl-4-oxo-2-imidazolidinylidene) urea;
3-m-ethylphenyl-1-(1-ethyl-4-oxo-2-imidazolidinylidene) urea;
1-(3,4-dimethylphenyl)-3-(1-methyl-4-oxo-2-imidazolidinylidene) urea, m.p. 219°–221° C dec;
1-(p-trifluoromethylphenyl)-3-(1-methyl-4-oxo-2-imidazolidinylidene) urea, m.p. 197°–200° C dec;
1-(p-t-butylphenyl)-3-(1-methyl-4-oxo-2-imidazolidinyl-idene) urea, m.p. 188°–189° C; and
1-(3-n-propylphenyl)-3-(1-methyl-4-oxo-2-imidazolidinylidene) urea, m.p. 167°–168° C.

EXAMPLE XIII 1-(3-Chlorophenyl)-3-(1,3-dimethyl-4-oxo-3-imidazolidinylidene) urea A mixture of 6.35 g (0.050 mole) of 1,3-dimethyl-2-iminoimidazolidin-4-one, 7.85 g (0.050 mole) of 3-chlorophenylisocyanate and 75 ml of dry tetrahydrofuran is stirred at room temperature for 4 hours. The solution is evaporated in vacuo and the residue is crystallized from acetonitrile. Two recrystallizations from acetonitrile - ether gives pure product, 1-(3-chlorophenyl)-3-(1,3-dimethyl-4-oxo-2-imidazolidinylidene)urea, m.p. 134°–137° C.

EXAMPLE XIV 1-(3-Chloro-2,6-dimethylphenyl)-3-(1-methyl-4-oxo-2-imidazolidinylidene) urea To a stirring suspension of 7.92 g (0.07 mole) of creatinine in 50 ml of dry DMF is added 9.08 g (0.05 mole) of 3-chloro-2,6-dimethylphenyl isocyanate. After stirring for 4 hours, the reaction mixture is filtered through a diatomaceous earth pad to remove unreacted creatinine. Addition of a large excess of ice water precipitates a gummy semisolid mass which eventually crystallizes. After blowing the product to dry it for about 18 hours, it is recrystallized from acetone-ether. Finally the product is taken up in dichloromethane and the resulting solution is filtered through diatomaceous earth. Concentration and dilution with ether gives pure product, 1-(3-chloro-2,6-dimethylphenyl)-3-(1-methyl-4-oxo-2-imidazolidinylidene) urea; m.p. 140°–141.5° C.

EXAMPLE XV 1-(2,6-dimethylphenyl)-3-(5,5-diphenyl-4-oxo-2-imidazolidinylidene) urea A suspension of 6.95 g (0.0306 mole) of 5,5-diphenyl-2-amino-2-imidazoline-4-one in 300 ml of dry DMF is treated with 4.5 g (0.0306 mole) of 2,6-dimethylphenylisocyanate. The reaction mixture is stirred at 40° C for 2 hours. It is then poured into cold water and the resulting solids are filtered off. To the crude product is added 30 ml of water with heating; acetone is added to the heated slurry until all solids go in solution (1.5 liters of acetone). The solution is then evaporated to a volume of 300 ml., chilled, and the resulting solids are filtered off to give 1-(2,6-dimethylphenyl)-3-(5,5-diphenyl-4-oxo-2-imidazolidinylidene) urea, the product; no m.p. up to 350° C.
Analysis: Calcd. for $C_{24}H_{22}N_4O_2$: C, 72.32; H, 5.56%. Found: C, 72.00; H, 5.68%.

EXAMPLE XVI 1-(1,3-Dimethyl-4-oxo-2-imidazolidinylidene)-3-(2,6-dimethylphenyl) urea A mixture of 6.35 g (0.050 mole) of 1,3-dimethyl-2-iminoimidazolidin-4-one and 7.25 g (0.050 mole) of 2,6-dimethylphenylisocyanate in 75 ml. of dry tetrahydrofuran is stirred at room temperature for 2 hours followed by refluxing it for 30 minutes. The reaction mixture is evaporated in vacuo to give a solid, which is crystallized from tetrahydrofuran-ether. Two more recrystallizations from the same solvent mixture gives pure product, 1-(1,3-dimethyl-4-oxo-2-imidazolidinylidene)-3-(2,6-dimethylphenyl) urea; m.p. 115.5°–118.5° C.

EXAMPLE XVII

Following the procedure of Example XVI, but substituting equivalent amounts of an appropriate imidazolidin-4-one and an appropriate arylisocyanate for the 1,3-dimethyl-2-iminoimidazolidin-4-one and 2,6-dimethylphenylisocyanate used therein, the following respective products are obtained:

1-(3-chlorophenyl)-3-(1-octyl-4-oxo-2-imidazolidinylidene) urea, m.p. 98°–100° C;
1(1-octyl-4-oxo-2-imidazolidinylidene)-3-phenylurea, m.p. 109.5°–110° C;
1-(3-chlorophenyl)-3-(1-methyl-4-oxo-5-benzyl-2-imidazolidinylidene)urea, m.p. 167°–168° C; and
1-(1-methyl-4-oxo-5-benzyl-2-imidazoidinylidene)-3-phenylurea, m.p. 158°–160° C.

EXAMPLE XVIII 1-(1-Methyl-4-oxo-2-imidazolidinylidene)-3-m-nitrophenyl urea

To a stirred slurry of 12.45 g (0.11mole) of creatinine in 100 ml of dry DMF is added 16.41 g (0.1 mole) of m-nitrophenyl isocyanate (previously recrystallized from benzene-pentane). After 9 hours, ice water is gradually added until crystallization occurres. A large excess of ice water precipitates the product as gummy crystals which then crystallize. The crude product is allowed to air dry for several days. Recrystallization from $THF-H_2O$ followed by THF gives pure product, 1-(1-methyl-4-oxo-2-imidazolidinylidene)-3-m-nitrophenyl urea; m.p. 182°–188° C sl. dec.

EXAMPLE XIX

Following the procedure of Example XVIII, but substituting an equivalent amount of an appropriate arylisocyanate for the m-nitrophenylisocyanate used therein, the following respective products are obtained:

1-(1-methyl-4-oxo-2-imidazolidinylidene)-3(p-nitrophenyl)urea, m.p. 220°–223° C dec; and
1-(p-dimethylaminophenyl)-3-(1-methyl-4-oxo-2-imidazolidinylidene)urea; m.p. 210°–216° C dec.

EXAMPLE XX

Following the procedure of Example X, but substituting equivalent amounts of an appropriate imidazolidin-4-one and an appropriate arylisocyanate for the creatinine and 2,6-xylylisocyanate used therein, the following respective products are obtained:

1-(3-chlorophenyl)-3-(3-methyl-4-oxo-2-imidazolidinylidene) urea; m.p. 169°–171° C; and
1-(3-chlorophenyl)-3-(5,5-diphenyl-4-oxo-2-imidazolidinylidene)urea; m.p. 274°–277° C.

EXAMPLE XXI

Following the procedure of Example I, but substituting an equivalent amount of 2-imino-1-methyl-hexahydropyrimidin-4-one for the creatinine used therein, 1-(1-methyl-4-oxo-2-hexahydropyrimidinylidene)-3-p-chlorophenyl urea is prepared.

EXAMPLE XXII

Following the procedure of Example X, but substituting an equivalent amount of 2-imino-1-1-methyl-hexahydropyrimidin-4-one for the creatinine used therein, 1-(1-methyl-4-oxo-2-hexahydropyrimidinylidene)-3-(2,6-xylyl) urea is prepared.

EXAMPLE XXIII

Following the procedure of Example VI, but substituting equivalent amounts of 2-imino-1-methyl-hexahydropyrimidin-4-one and appropriate aryl isocyanate for the creatinine and p-chlorophenylisocyanate used therein, the following are prepared:

1-(1-methyl-4-oxo-2-hexahydropyrimidinylidene)-3-(p-ethoxyphenyl) urea;
1-(1-methyl-4-oxo-2-hexahydropyrimidinylidene)-3-(p-dimethylaminophenyl) urea; and
1-(1-methyl-4-oxo-2-hexahydropyrimidinylidene)-3-(p-nitrophenyl) urea.

The above examples are intended to illustrate, but not to limit, the scope of the present invention, which is defined in the following claims.

What is claimed is:

1. A 4-oxo-2-hexahydropyrimidinylidene urea having the formula

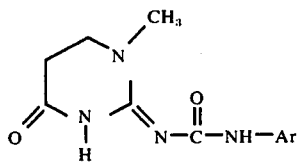

wherein Ar is a member selected from the group consisting of phenyl, nitrophenyl, trifluoromethylphenyl, diloweralkylaminophenyl, and phenyl substituted with from one to three members each selected from the group consisting of halo, loweralkyl, and loweralkoxy.

* * * * *

UNITED STATES PATENT AND TRADEMARK OFFICE
CERTIFICATE OF CORRECTION

PATENT NO. : 4,025,517
DATED : May 24, 1977
INVENTOR(S) : Rasmussen

It is certified that error appears in the above-identified patent and that said Letters Patent are hereby corrected as shown below:

In Column 3, line 44, "it put into" should read ---is put into---
In Column 3, line 68, "0.01 NaOH." should read ---0.01N NaOH.---
In Column 4, line 61, "anti-syrychnine" should read
---anti-strychnine---
In Column 6, line 42, "4.16" should read ---4.16%---
In Column 8, line 32, "4-oxoimidazolidene)" should read
---4-oxoimidazolidinylidene)---
In Column 8, line 34, "(260.39)" should read ---(260.30)---
In Column 9, line 3, "4-oxo-3-" should read "4-oxo-2-"
In Column 9, line 49, "the product;" should read
---the pure product;---
In Column 10, line 67, "2-imino-1-1-methyl" should read
"2-imino-1-methyl"

Signed and Sealed this

Eighth Day of August 1978

[SEAL]

Attest:

RUTH C. MASON
Attesting Officer

DONALD W. BANNER
Commissioner of Patents and Trademark